United States Patent
Loyns et al.

(10) Patent No.: US 9,133,288 B2
(45) Date of Patent: Sep. 15, 2015

(54) RETARDER COMPOSITION

(75) Inventors: Colin Loyns, Sheffield (GB); Andrew Nigel Fawbert, Brighouse (GB); Angela Jane Glossop, Rotherham (GB); Peter Mark Price, Ilkley (GB)

(73) Assignee: NUFARM UK LIMITED, Yorkshire (GB)

( * ) Notice: Subject to any disclaimer, the term of this patent is extended or adjusted under 35 U.S.C. 154(b) by 252 days.

(21) Appl. No.: 13/808,924

(22) PCT Filed: Jul. 8, 2011

(86) PCT No.: PCT/GB2011/051277
§ 371 (c)(1),
(2), (4) Date: Jan. 8, 2013

(87) PCT Pub. No.: WO2012/004605
PCT Pub. Date: Jan. 12, 2012

(65) Prior Publication Data
US 2013/0116486 A1    May 9, 2013

(30) Foreign Application Priority Data
Jul. 9, 2010    (GB) .................................. 1011594.7

(51) Int. Cl.
```
C07C 2/04      (2006.01)
C07C 2/06      (2006.01)
C09K 15/08     (2006.01)
C09K 15/24     (2006.01)
C08F 12/08     (2006.01)
C07C 7/20      (2006.01)
C08F 2/40      (2006.01)
C08F 12/36     (2006.01)
C09K 15/20     (2006.01)
C08K 5/08      (2006.01)
C08K 5/32      (2006.01)
```

(52) U.S. Cl.
CPC . C08F 12/08 (2013.01); C07C 7/20 (2013.01); C08F 2/40 (2013.01); C08F 12/36 (2013.01); C09K 15/08 (2013.01); C09K 15/20 (2013.01); C08K 5/08 (2013.01); C08K 5/32 (2013.01)

(58) Field of Classification Search
USPC ........... 585/428, 502, 520; 252/403, 404, 405
See application file for complete search history.

(56) References Cited

U.S. PATENT DOCUMENTS

| | | |
|---|---|---|
| 4,434,307 A | 2/1984 | Miller |
| 5,648,573 A | 7/1997 | Arhancet et al. |
| 5,773,674 A | 6/1998 | Arhancet et al. |
| 2002/0037958 A1 | 3/2002 | Benage et al. |
| 2003/0047439 A1 | 3/2003 | Benage et al. |
| 2005/0113625 A1* | 5/2005 | Benage et al. ................. 585/950 |

FOREIGN PATENT DOCUMENTS

| | | |
|---|---|---|
| EP | 0240297 A1 | 10/1997 |
| WO | 9641783 A1 | 6/1996 |
| WO | 0014177 A1 | 3/2000 |
| WO | 0140404 A1 | 6/2001 |
| WO | 2006138034 A1 | 12/2006 |

OTHER PUBLICATIONS

J.W. Breitenbach; B. Wolf, Untersuchungen über Molekulargewichtsverteilungen von Hochpolymeren, 5. Mitt.: Thermische Styrolpolymerisate bei Verzögerung durch Thymochinon:, Monatshefte Für Chemie, 1964, pp. 508-511, vol. 95, No. 2.

* cited by examiner

*Primary Examiner* — Thuan D Dang

(74) *Attorney, Agent, or Firm* — E. Eric Mills; Nexsen Pruet, PLLC

(57) ABSTRACT

The invention relates to a retarder composition for the control of unwanted polymerization reactions during the production and processing of ethylenically unsaturated compounds, the composition comprising at least one di-substituted quinone compound and at least one hydroxylamine compound. Optionally, the composition also comprises at least one stable free radical nitroxyl compound and one or more formulation adjuvants. The invention also envisages a process stream comprising at least one ethylenically unsaturated compound, and a method for the prevention of unwanted polymerization reactions during the production and processing of ethylenically unsaturated compounds. The composition has been found to be far more effective than expected, given that the individual components show little or no efficacy when used alone, and poses much less hazard to humans than the compositions of the prior art.

22 Claims, No Drawings

RETARDER COMPOSITION

FIELD OF THE INVENTION

The present invention relates to the production and processing of ethylenically unsaturated monomers. More specifically, it provides a composition and method which is useful for the retardation of unwanted polymerisation reactions during the production and processing of said monomers.

BACKGROUND TO THE INVENTION

During the industrial production of vinyl aromatic monomers or other ethylenically unsaturated monomers there is usually a requirement for high temperature processing operations, such as purification by fractional distillation, and the performance of said operations at elevated temperatures can often cause unwanted thermal polymerisation of the monomer. The thus formed polymer is a problem economically, and can also give rise to safety and process efficiency issues which adversely affect the monomer processing operation.

Economic loss occurs because the yield of valuable monomer is reduced due to polymerisation of the monomer to form a polymer which is merely valued, at best, on its calorific content as a fuel, whilst the process efficiency and safety problems are associated with the tendencies of the polymer to foul surfaces such as heat transfer surfaces, and to cause blockages to flow through the equipment or to increase the viscosity of process streams, so that flux oil or valuable monomer has to be added in order to reduce the viscosity and thereby enable the process stream to be moved readily by gravity, or by forced flow such as by pumping.

In order to control such unwanted polymerisation it is common practice to employ an anti-polymerant composition in the process stream. These anti-polymerant compositions essentially fall into one of two categories, namely inhibitors and retarders.

Inhibitors are effective in preventing the formation of polymer, but they are substantially consumed in this process. This consumption can cause problems in situations where the inhibitor cannot be replenished, for example because of feed pump failure. Consequent to the inhibitor being consumed there is a loss of the means of control of the polymerisation and, thus, rapid polymerisation can then occur.

Retarders, on the other hand, may be less effective than inhibitors in limiting the amount of polymerisation, but they do have the advantage that they are not substantially consumed under their conditions of use. Retarders are, therefore, more reliable because they are longer acting and they provide some security in situations where unplanned circumstances arise.

The prior art discloses many different compositions for use in controlling the extent of the unwanted polymerisation of ethylenically unsaturated monomers. However, very few of the prior art compositions possess the desirable characteristics of a polymerisation retarder and those that do display such characteristics are also associated with other properties which are disadvantageous.

Thus, for example, DD-A-234020 teaches the use of compositions containing phenols, whilst U.S. Pat. No. 4,654,451 discusses nitrosophenolic compounds. Phenylenediamine compounds are disclosed in U.S. Pat. No. 4,774,374, whilst U.S. Pat. No. 4,252,615 and U.S. Pat. No. 4,086,147 are both concerned with the use of nitrophenols. SU-A-819078 and EP-A-550754 describe the use of quinine methides for this purpose, and nitroxyl compounds are the focus of JP-A-01165534, GB-A-1127127 and CS-B-260755. In addition, the use of quinones is considered in JP-A-5085964, which discloses employing p-benzoquinone as a retarder, whilst JP-A-63235390 teaches methods which are based on the incorporation of alkylated quinones, naphthaquinones and anthraquinones for the control of unwanted polymerisation.

However, none of these prior art compositions fulfils all the requirements of efficacy and ease of use which are the desired attributes of a successful composition for the control of the degree of polymerisation of ethylenically unsaturated monomers during their production and processing. Consequently many subsequent attempts have been made by other workers to improve upon these aspects by means of compositions which contain at least two of these known substances. Thus, for example, processes are disclosed in U.S. Pat. No. 4,929,778 which require the use of a combination of phenylene diamines and hindered phenols, whilst mixtures of nitrophenols and hydroxylamines are considered in EP-A-240297, nitrophenols and nitroxyl compounds in U.S. Pat. No. 5,254,760, quinones and nitroxyl compounds in US-A-2002/0037958, quinones and hydroxylamines in WO-A-96/41783, and CN-A-1962582 teaches a mixture of a quinone with a nitrophenol and a nitrite.

Nevertheless, despite these efforts, even these more sophisticated compositions fail to provide all the desired characteristics of a successful polymerisation retarder composition for use in the control of the amount of unwanted polymerisation under the process conditions which are typically encountered, and there remains a need for an improved polymerisation retarder composition, most particularly for use in controlling the amount of polymerisation which occurs during the production and processing of ethylenically unsaturated monomers.

The desired characteristics of such a composition include a low potential for harm to humans, as well as a high efficacy of control of the amount of polymerisation under the process conditions. The conditions which prevail during the industrial processing of ethylenically unsaturated monomers can involve the use of elevated temperatures, for example up to about 140° C., for extended periods, e.g. two hours or more, and with low or very low oxygen levels.

Furthermore, due to the complex nature of such processing plants, non-standard operating conditions of temperature, dwell time and oxygen content can occur from time to time, thereby resulting in greater than normal reliance on the polymerisation control composition. The non-standard conditions can also involve an interruption in the flow of the polymerisation control composition into the ethylenically unsaturated monomer process stream, which may occur, for example, because a distillation column needs to be run under total reflux for a period of time. In such an event, it is a requirement of the polymerisation control composition that its efficacy should not be quickly exhausted, but that it should continue to give control over the whole duration of the period of the non-standard operating conditions. Such long-lasting polymerisation control properties can be provided by a retarder composition, whereas inhibitors do not have such longevity of efficacy and can be found to become ineffective too quickly to be useful.

It has been established that the polymerisation retarder compositions of the prior art containing phenols such as methyl pyrocatechol, cresols or xylenols, or those containing phenylenediamine compounds such as N-isopropyl-N'-phenyl-p-phenylenediamine, are relatively ineffective at controlling the amount of polymerisation of ethylenically unsaturated compounds when there is low or very low oxygen content prevailing during the processing of ethylenically unsaturated monomers. The consequence of this poor efficacy is an unacceptable economic loss of the vinyl aromatic monomer due to unwanted polymerisation. Furthermore, whilst nitroxyl compounds such as 4-amino-2,2,6,6-tetra methyl piperidine-N-oxyl (amino tempo) and 4-hydroxy-2,2,6,6-tetra methyl piperidine-N-oxyl (hydroxy tempo) are known to be very effective components of compositions for controlling the amount of unwanted polymerisation of ethylenically unsaturated monomers at low and intermediate temperatures (e.g. up to about 100° C.), their efficacy decreases with increasing temperature such that, above about 120° C., they cease to control the amount of polymerisation and merely modify the characteristics of the polymer which is formed. Furthermore, it is found that these nitroxyl compounds are inhibitors rather than retarders. Therefore, nitroxyl compounds do not have the persisting action required for controlling the amount of polymerisation in the event of, for example, a period of total reflux operation.

Other chemical types, such as quinone methides and Mannich base compounds, can be used to provide non-toxic retarder compositions, but they are effective only at lower operating temperatures, such as up to about 110° C. When they are used at temperatures in excess of this they become ineffectual and the doses required are too high to be economically viable when compared to current commercially employed nitrophenol-based retarder compositions.

Nitrophenol compounds such as 2,4-dinitro-ortho-cresol (DNOC), 2,6-dinitro-para-cresol (DNPC), 2,4-dinitro-phenol (DNP) or 2,4-dinitro-ortho-sec-butyl-phenol (DNBP or "Dinoseb") are known to be effective components of polymerisation retarder compositions for controlling the polymerisation of vinyl aromatic monomers under the above mentioned conditions. These nitrophenols are particularly effective as retarders and so they are the most frequently used class of material in commercial use for controlling the amount of thermal polymerisation of vinyl aromatic monomers in processing plants. However, these nitrophenols are toxic materials with potential to cause harm to humans and to the environment. Similarly, the nitrosophenolic compounds, such as paranitrosophenol, are found to be effective components of retarder compositions, but such aromatic nitroso compounds are solid products with poor solubility characteristics, and they are therefore difficult to handle; in addition, the toxicity properties of these compounds are such that they also have potential to cause harm to humans.

Commercial operations engaged in operating vinyl aromatic monomer process plants prefer not to handle and use toxic materials for health and safety reasons. Instead, they seek to employ non-toxic materials in order to obtain the very evident benefits of promoting the health and welfare of their employees and protecting the environment. Furthermore, in view of their undesirable toxicity properties, these nitrophenols and nitrosophenols are increasingly becoming subject to regulatory actions by national and international authorities in order to restrict or prevent their commercial supply. Consequently, it is likely that such nitrophenols and nitrosophenols might cease to be available for commercial use in polymerisation control compositions in the future.

WO-A-96/41783 discloses compositions and methods of use of specified quinones and specified hydroxylamines for inhibiting the polymerisation of vinyl aromatic monomers. However, the compositions disclosed in WO-A-96/41783 are characterisable as inhibitors and they do not possess the desirable longer term protection attributes of a retarder.

In view of the problems which are associated with the polymerisation control compositions of the prior art, there exists a need for new, effective and non-toxic, polymerisation retarder compositions, which specifically do not contain materials which are toxic to humans, for use in controlling the amount of unwanted polymerisation of ethylenically unsaturated monomers during their production and processing. Thus, the present invention seeks to provide new polymerisation retarder compositions which offer significant improvement over the prior art compositions in terms of efficacy in use, long lasting activity, and low toxicity.

SUMMARY OF THE INVENTION

The present inventors have now developed polymerisation retarder compositions, and methods for the use thereof, wherein the compositions possess all the desirable attributes for the control of the amount of unwanted polymerisation of vinyl aromatic monomers and other ethylenically unsaturated monomers, whilst not displaying the disadvantageous features of the compositions of the prior art. Most particularly, the compositions of the present invention possess long-lasting retarder type activity with a high efficacy of control of the amount of polymerisation under the process conditions of the monomer, and also display low potential for harm to humans.

Thus, according to a first aspect of the present invention there is provided a retarder composition for the prevention of unwanted polymerisation reactions during the production and processing of ethylenically unsaturated compounds, said composition comprising:

(a) at least one quinone compound of structure (i):

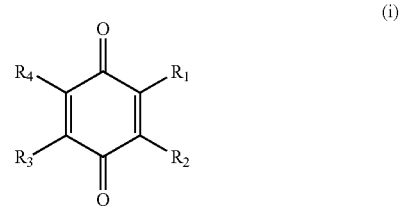

(i)

and
(b) at least one hydroxylamine of structure (ii):

(ii)

wherein:
$R_1$ and $R_3$ are each independently selected from the group consisting of $C_1$, $C_2$, $C_3$, $C_4$, $C_5$, $C_6$, $C_7$ or $C_8$ straight or branched chain saturated or unsaturated hydrocarbons and optionally substituted phenyl and benzyl, and wherein $R_2$ and $R_4$ are H;

$R_5$ to $R_6$ are each independently selected from the group consisting of $C_1$, $C_2$, $C_3$, $C_4$, $C_5$, $C_6$, $C_7$ or $C_8$ straight or branched chain saturated or unsaturated hydrocarbons or hydroxyhydrocarbons and $C_5$, $C_6$ or $C_7$ saturated or unsaturated hydrocarbon rings which may optionally be substituted, and arylakyls which may optionally be substituted on the aryl moiety and wherein the alkyl moiety comprises $C_1$, $C_2$, $C_3$ or $C_4$ straight or branched chain hydrocarbons, and wherein the aryl moiety comprises one or more rings which are optionally substituted and in the case of more than one ring these may include fused rings.

Optionally, said composition may also comprise:
(c) at least one stable free radical nitroxyl compound of structure (iii):

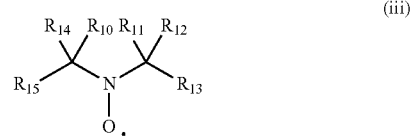

(iii)

wherein:
$R_{10}$ to $R_{15}$ are each independently selected from the group comprising $C_1$, $C_2$, $C_3$, $C_4$, $C_5$, $C_6$, $C_7$ or $C_8$ straight or branched chain saturated or unsaturated hydrocarbons and $C_5$, $C_6$ or $C_7$ saturated or unsaturated hydrocarbon rings, and $R_{10}$ plus $R_{11}$ may together form a saturated or unsaturated ring optionally containing a further hetero atom, wherein the ring is optionally further substituted with one or more branched or straight chain alkyl or alkenyl groups or one or more moieties selected from hydroxyl, oxyl, amino and alkoxyl, and wherein two or more such nitroxyl containing rings may be joined by any linking groups, examples of which include $C_1$ to $C_{18}$ alkylene, $C_4$ to $C_{18}$ alkenylene, xylylene, a divalent acyl radical of an aliphatic, araliphatic or aromatic dicarboxylic acid or of a dicarbamic acid or of a phosphorous-containing acid or of a sulphur containing acid or a bivalent silyl radical or a sulphone, a sulphide or a nitrogen containing group or a bisether, and preferred examples of which are an acyl radical of an aliphatic $C_2$ to $C_{36}$ dicarboxylic acid, or of a $C_8$ to $C_{14}$ cycloaliphatic acid or of a $C_8$ to $C_{14}$ aromatic dicarboxylic acid, or of a $C_8$ to $C_{14}$ aromatic dicarbamic acid.

In said compositions, the preferred weight ratio of component (a) (comprising at least one compound of structure (i)) to component (b) (comprising at least one compound of structure (ii)) is in the range of from 9:1 to 1:9.

Optionally, said compositions may also contain one or more formulation adjuvants selected from the known classes of solvents, solubilising agents, liquid carrying agents, emulsifiers and dispersants.

Typically, the ethylenically unsaturated compounds associated with the present invention comprise vinyl aromatic monomers or other ethylenically unsaturated monomers.

A second aspect of the present invention envisages a process stream which comprises a retarder composition according to the first aspect of the invention in combination with at least one ethylenically unsaturated compound, which typically comprises a vinyl aromatic monomer or other ethylenically unsaturated monomer. In such process streams, it is preferred that the weight ratio of retarder composition (comprising components (a), (b) and optionally (c)) to ethylenically unsaturated compound is in the range of from 1:200 to 1:40000.

According to a third aspect of the present invention, there is provided a method for the prevention of unwanted polymerisation reactions during the production and processing of ethylenically unsaturated compounds, said method comprising treating a composition comprising at least one ethylenically unsaturated compound with a composition according to the first aspect of the invention.

DESCRIPTION OF THE INVENTION

The present invention provides compositions of quinones (i) and hydroxylamines (ii) which provide the desirable properties of a polymerisation retarder. Specifically, the quinones disclosed in the context of the present invention differ from those which are taught in WO-A-96/41783, such that the compositions of the present invention surprisingly possess the desirable properties of retarders, whereas those of WO-A-96/41783 merely function as inhibitors.

Most particularly, the present invention provides compositions having the desirable properties of a polymerisation retarder, and which comprise at least one quinone and at least one hydroxylamine wherein the quinone has two substituents in the ring and in specific positions in the ring, whereas the compositions of WO-A-96/41783 comprise a quinone and a hydroxylamine wherein the quinone is at most mono-substituted in the ring. It is surprisingly and unexpectedly found that the quinone compounds utilised in the compositions of the present invention confer retarder properties in compositions wherein they are combined with the specified hydroxylamines.

The compositions of the present invention contain at least one quinone compound (i) and at least one hydroxylamine compound (ii) and optionally at least one stable free radical compound (iii) and one or more formulation adjuvants of the type and quantity known to a skilled person for the purpose of preparing a stable mixture thereof. The invention also envisages process streams which additionally comprise at least one ethylenically unsaturated compound, preferably comprising at least one vinyl aromatic monomer or other ethylenically unsaturated monomer.

The quinone compounds which are useful in the compositions and method of the present invention are in the group of quinones of the general formula (i):

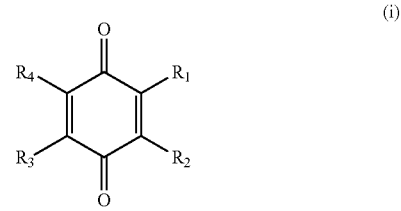

(i)

wherein:
$R_1$ and $R_3$ are each independently selected from the group comprising $C_1$, $C_2$, $C_3$, $C_4$, $C_5$, $C_6$, $C_7$ or $C_8$ straight or branched chain saturated or unsaturated hydrocarbons and optionally substituted phenyl and benzyl, and wherein $R_2$ and $R_4$ are H.

Preferred quinones for use in the context of the present invention are 2,5-di-alkyl substituted benzoquinones and, most preferably, the di-substituted benzoquinone is 2,5-di-tert-butylbenzoquinone.

The hydroxylamines used in the compositions and method of the present invention are selected from the group of structures (ii):

(ii)

wherein:
$R_5$ to $R_6$ are each independently selected from the group comprising $C_1$, $C_2$, $C_3$, $C_4$, $C_5$, $C_6$, $C_7$ or $C_8$ straight or branched chain saturated or unsaturated hydrocarbons or hydroxyhydrocarbons and $C_5$, $C_6$ or $C_7$ saturated or unsaturated hydrocarbon rings which may optionally be substituted rings, and arylakyls which may optionally be substituted on the aryl moiety and wherein the alkyl moiety comprises $C_1$, $C_2$, $C_3$ or $C_4$ straight or branched chain hydrocarbons and wherein the aryl moiety comprises one or more rings which are optionally substituted and, in the case of more than one ring, these may include fused rings.

Hydroxylamines which are useful in the compositions according to the first aspect of the invention include aliphatic hydroxylamines such as bis(hydroxypropyl)hydroxylamine. Preferred hydroxylamines, however, are aromatic hydroxylamines, and a particularly preferred aromatic hydroxylamine is N,N-dibenzyl hydroxylamine.

Compositions of the present invention may also optionally contain one or more nitroxyl compounds of formula (iii):

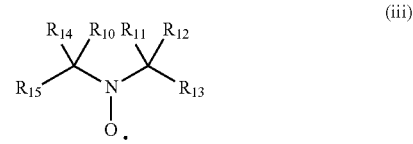

(iii)

wherein:
$R_{10}$ to $R_{15}$ are each independently selected from the group comprising $C_1$, $C_2$, $C_3$, $C_4$, $C_5$, $C_6$, $C_7$ or $C_8$ straight or branched chain saturated or unsaturated hydrocarbons and $C_5$, $C_6$ or $C_7$ saturated or unsaturated hydrocarbon rings, and $R_{10}$ plus $R_{11}$ may together form a saturated or unsaturated ring optionally containing a further hetero atom, wherein the ring is optionally further substituted with one or more branched or straight chain alkyl or alkenyl groups or one or more moieties selected from hydroxyl, oxyl, amino and alkoxyl, and wherein two or more such nitroxyl containing rings may be joined by any linking groups.

Examples of suitable linking groups include $C_1$ to $C_{18}$ alkylene, $C_4$ to $C_{18}$ alkenylene, xylylene, a divalent acyl radical of an aliphatic, araliphatic or aromatic dicarboxylic acid or of a dicarbamic acid or of a phosphorous-containing acid or of a sulphur containing acid or a bivalent silyl radical or a sulphone, a sulphide or a nitrogen containing group or a bisether.

Preferred linking groups include, for example, an acyl radical of an aliphatic $C_2$ to $C_{36}$ dicarboxylic acid, or of a $C_8$ to $C_{14}$ cycloaliphatic acid or of a $C_8$ to $C_{14}$ aromatic dicarboxylic acid or of a $C_8$ to $C_{14}$ aromatic dicarbamic acid.

Preferred nitroxyl compounds are 4-hydroxy-2,2,6,6-tetramethylpiperidin-N-oxyl and 4-oxo-2,2,6,6-tetramethylpiperidin-N-oxyl.

Compositions of the present invention also optionally contain one or more formulation adjuvants, said adjuvants being selected from the known classes of solvents, cosolvents, solubilising agents, liquid carrying agents, emulsifiers and dispersants. Typical solvents or cosolvents or liquid carrying agents include aromatic solvents, for example ethyl benzene, and vinyl aromatics, for example styrene monomer, and non-aromatic solvents, for example alcohols or glycol ethers, exemplified by the alkyl ethers of diethylene glycol.

The compositions of the present invention find application in the prevention of unwanted polymerisation reactions during the production and processing of ethylenically unsaturated compounds typically comprising vinyl aromatic monomers or other ethylenically unsaturated monomers, and are added to a process stream thereof. Typical vinyl aromatic monomers which are present in such process streams include, for example, styrene monomer, divinyl benzene and the like. Other ethylenically unsaturated monomers include acrylonitrile, (meth)acrylic acid and esters thereof, butadiene, isoprene and the like.

The method of the present invention may be carried out by any of the standard techniques well known in the art, for example by injecting into a process stream one or more quinones as hereinbefore defined and one or hydroxylamines as hereinbefore defined, either separately or together, e.g. by premixing the quinone and the hydroxylamine, with or without the addition of one or more adjuvants for the purpose of enabling a stable mixture thereof, for example one or more carrier solvents and/or co-solvents as hereinbefore defined. In the case that the quinone and the hydroxylamine are injected separately, either or both of the quinone and the hydroxylamine may be in the form of a liquid formulation in one or more solvents or carrier liquids as hereinbefore defined.

The composition and method of the present invention will now be further illustrated, though without in any way limiting the scope of the invention, by reference to the following examples.

Examples

Laboratory tests were carried out in order to demonstrate the effectiveness of various individual substances and compositions thereof for controlling the amount of unwanted polymerisation of an ethylenically unsaturated compound. The particular ethylenically unsaturated compound used in the tests was a vinyl aromatic monomer, specifically styrene monomer. The use of a vinyl aromatic monomer for this purpose is illustrative and is not intended to exclude other ethylenically unsaturated compounds from the scope of this invention.

Batch tests (the results of which are detailed in Table 1), and continuous flow tests (the results of which are presented in Table 2) were carried out in order to represent different types of processing conditions which can occur in the industrial processing of ethylenically unsaturated compounds. These tests compare the compositions of the present invention with compositions of the prior art. DNBP (2,4-dinitro-ortho-sec-butyl-phenol) is the polymerisation retarder of the prior art most commonly employed in commercial production of vinyl aromatic monomers.

The following abbreviations are used hereinafter:

| | |
|---|---|
| BQ = benzoquinone | DNBP = Dinoseb |
| DBHA = N,N-dibenzyl hydroxylamine | HPHA = bishydroxypropylhydroxylamine |
| Me = methyl benzoquinone | Tetra-me = tetramethylbenzoquinone |
| 2-t-bu = 2-tert-butyl benzoquinone | 2,3,5-tri = 2,3-dimethoxy-5-methylbenzoquinone |
| 2,5-di-me = 2,5-dimethyl benzoquinone | 2,5-di-t-bu = 2,5 di-tert-butylbenzoquinone |
| 2,6-di-me = 2,6-dimethyl benzoquinone | 2,6-di-t-bu = 2,6 di-tert-butylbenzoquinone |

Batch Tests

The batch test was designed in order to show whether a test composition is an inhibitor or a retarder. The tests were carried out in styrene monomer refluxing under reduced pressure at 120° C. in order to reduce the presence of atmospheric oxygen to such low levels as can be expected in a commercial styrene monomer purification plant.

For the batch tests the vinyl aromatic monomer composition containing the test substances was heated to 120° C. and stirred under reduced pressure so that it refluxed at the test temperature. Samples were taken at intervals of time and tested for polymer content in order to assess the effectiveness of polymerisation control. The results are presented in Table 1.

These batch test results demonstrate the longevity of the anti-polymerant composition and, therefore, this test is capable of distinguishing between inhibitors—which are consumed relatively quickly—and retarders, which have a longer time period of effectiveness.

The results set out in Table 1 confirm that DNBP (Control 1) has long term effectiveness and is therefore a retarder. However, Controls 2 and 3 are compositions representing the prior art disclosed in WO-A-96/41783, and they are shown not to have a long term effectiveness and, consequently, are inhibitors.

Controls 5 and 6 involve individual components of the composition of the present invention, namely a 2,5-disubstituted benzoquinone and a hydroxylamine. The results show that neither of these two substances has any significant polymerisation control effect when used alone. In other words, when used alone these substances are neither inhibitors nor retarders. It is therefore surprising that the compositions of the present invention, involving the use of such substances in combination, demonstrate any activity as polymerisation retarder compositions, let alone that such combinations such a marked synergistic effect. Indeed, such synergy is completely unexpected.

Tests 1 to 7 involve compositions of the present invention, and demonstrate good polymerisation retarding properties. Indeed, the compositions of Tests 1 to 7 have a retarder action which is even superior to that of DNBP, the material most commonly employed in the vinyl aromatic monomer processing industry. Furthermore, the level of performance demonstrated by the compositions of the present invention is so good that less polymer is obtained when compared to the DNBP control even in circumstances when a significantly lower dose of the compositions of the present invention is used.

Tests 8 to 11 are illustrative of compositions containing benzoquinones which are outside the preferred range of benzoquinones which are used in the compositions and method of the present invention. They include 2,6-disubstituted quinones, and tri- and tetra-substituted quinones. In combination with the hydroxylamines which are used in the compositions and method of the present invention, such quinones act as inhibitors and, therefore, have similar action to that which is observed with the prior art compositions of WO-A-96/41783, even though they are also outside of the range of the compositions disclosed therein. It is evident, therefore, that the retarder effect of the compositions of the present invention is quite specific to the said compositions, and such specificity is surprising and would not have been expected by a skilled person.

It is clearly apparent from the results shown in Table 2 that, when the vinyl aromatic monomer composition contains both a substituted quinone and a hydroxylamine, according to the present invention, then the polymerisation retarding effect is better than that of DNBP to such an extent that only 60% of the dose of a composition of the present invention is required in comparison to the dose of DNBP necessary in order to achieve the same control of polymerisation. It is also noted that further reductions in polymer formation are achieved when a portion of the retarder composition is replaced with an inhibitor, such as hydroxy tempo. Thus, the compositions of the present invention are shown to have the desired efficacy

TABLE 1

BATCH TESTS

| Test No. | Component 1 (ppm) | Component 2 (ppm) | Polymer (ppm) @ (time) | | | Effect |
|---|---|---|---|---|---|---|
| | | | 30 mins | 150 mins | 180 mins | |
| Control 1 | DNBP (500) | | | | 6000 | Retarder |
| Control 2 | Benzoquinone Me (133) | Hydroxylamine DBHA (267) | | >6000 | | Inhibitor |
| Control 3 | 2-t-bu (200) | DBHA (400) | | >6000 | | Inhibitor |
| Control 4 | BQ (200) | DBHA (400) | | >10,000 | | Inhibitor |
| Control 5 | 2,5-di-t-bu (500) | None | >10,000 | | | None |
| Control 6 | None | DBHA (500) | >10,000 | | | None |
| 1 | 2,5-di-t-bu (250) | DBHA (250) | | | 4000 | Retarder |
| 2 | 2,5-di-t-bu (165) | DBHA (335) | | | 1000 | Retarder |
| 3 | 2,5-di-t-bu (133) | DBHA (267) | | | 4500 | Retarder |
| 4 | 2,5-di-t-bu (250) | HPHA (250) | | | 5000 | Retarder |
| 5 | 2,5-di-t-bu (212) | HPHA (288) | | | 6000* | Retarder |
| 6 | 2,5-di-t-bu (200) | DBHA (400) | | | 2400 | Retarder |
| 7 | 2,5-di-me (200) | DBHA (400) | | | 1000 | Retarder |
| 8 | 2,6-di-t-bu (200) | DBHA (400) | >4,000 | >10,000 | | Inhibitor |
| 9 | 2,6-di-me (200) | DBHA (400) | | 7,000 | | Inhibitor |
| 10 | 2,3,5-tri (133) | DBHA (267) | | >6000 | | Inhibitor |
| 11 | Tetra-me (133) | DBHA (267) | | >6000 | | Inhibitor |

*210 mins

Continuous Tests

In the case of the continuous tests as detailed in Table 2, a vinyl aromatic monomer composition containing a polymerisation retarder mixture was fed at a constant rate into a stirred vessel fitted with an outlet so that, by adjusting the feed rate and outlet rate, a dwell time of two hours in the vessel was achieved. After two dwell times (240 minutes) a so called "steady state" was reached, and the amount of polymer present became more or less constant, so that the test simulated the situation in a continuous distillation unit of an olefinic monomer production plant. The contents of the test vessel were maintained under reduced pressure, so that a steady reflux occurred at the test temperature. Samples were taken at intervals of time and tested for polymer content in order to assess the effectiveness of control of the amount of polymerisation. The examples set out in Table 2 involve styrene monomer, and the test temperature was 120° C.

TABLE 2

CONTINUOUS TESTS

| Experiment No. | Retarder (ppm) | Hydroxylamine (ppm) | Inhibitor (ppm) | Polymer at steady state (ppm) |
|---|---|---|---|---|
| Control 7 | DNBP 400 | 0 | 0 | 5000 |
| Control 8 | DNBP 500 | 0 | 0 | 1000 |
| 12 | 2,5-di-t-bu 150 | DBHA 150 | 0 | 4000 |
| 13 | 2,5-di-t-bu 100 | DBHA 200 | 0 | 1000 |
| 14 | 2,5-di-t-bu 133 | DBHA 267 | 0 | 570 |
| 15 | 2,5-di-t-bu 105 | DBHA 210 | Hydroxy tempo 35 | 450 | for controlling the amount of polymerisation which occurs when producing or processing vinyl aromatic monomers.

Furthermore, the compositions of the present invention do not contain substances which are toxic to humans and, consequently, they are of considerable benefit when compared to the formulations of the prior art that typically contain dinitrophenols such as DNBP which, as previously noted, is the material most commonly used in the vinyl aromatic monomer processing industry. A comparison of the properties of the substances utilised in the compositions of the current invention with those of the prior art material DNBP is provided in Table 3.

TABLE 3

COMPARISON OF HAZARD CLASSIFICATIONS

| | DNBP | DTBBQ | DBHA |
|---|---|---|---|
| Oral Toxicity | Yes | No | No |
| Dermal Toxicity | Yes | No | No |
| Toxic by Inhalation | Yes | No | No |

Thus, according to these hazard classifications, it is apparent that the components of the compositions of the present invention pose much less hazard to humans than does DNBP. As a consequence, the need to control the exposure of plant operators can be greatly reduced by using the compositions of the present invention instead of DNBP during production and processing operations using vinyl aromatic monomers. Thus, the compositions of the present invention provide both a more effective and a safer means of controlling unwanted polymerisation of vinyl aromatic monomers when compared to the compositions of the prior art.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A retarder composition for the prevention of unwanted polymerisation reactions during the production and processing of ethylenically unsaturated compounds, said composition comprising:

(a) at least one quinone compound of structure (i):

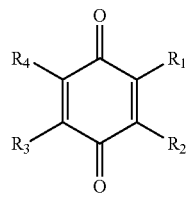

and
(b) at least one hydroxylamine of structure (ii):

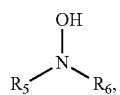

wherein:
$R_1$ and $R_3$ are each independently selected from the group consisting of $C_1$, $C_2$, $C_3$, $C_4$, $C_5$, $C_6$, $C_7$ or $C_8$ straight or branched chain saturated or unsaturated hydrocarbons and optionally substituted phenyl and benzyl, and wherein $R_2$ and $R_4$ are H;

$R_5$ to $R_6$ are each independently selected from the group consisting of $C_1$, $C_2$, $C_3$, $C_4$, $C_5$, $C_6$, $C_7$ or $C_8$ straight or branched chain saturated or unsaturated hydrocarbons or hydroxyhydrocarbons and $C_5$, $C_6$ or $C_7$ saturated or unsaturated hydrocarbon rings which may optionally be substituted, and arylakyls which may optionally be substituted on the aryl moiety and wherein the alkyl moiety comprises $C_1$, $C_2$, $C_3$ or $C_4$ straight or branched chain hydrocarbons, and wherein the aryl moiety comprises one or more rings which are optionally substituted and in the case of more than one ring these may include fused rings.

2. A composition as claimed in claim 1 wherein said composition also comprises:
(c) at least one stable free radical nitroxyl compound of structure (iii):

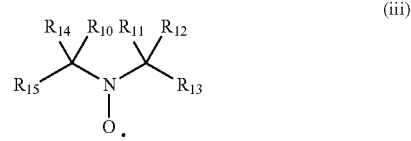

wherein:
$R_{10}$ to $R_{15}$ are each independently selected from the group consisting of $C_1$, $C_2$, $C_3$, $C_4$, $C_5$, $C_6$, $C_7$ or $C_8$ straight or branched chain saturated or unsaturated hydrocarbons and $C_5$, $C_6$ or $C_7$ saturated or unsaturated hydrocarbon rings, and $R_{10}$ plus $R_{11}$ may together form a saturated or unsaturated ring optionally containing a further hetero atom, wherein the ring is optionally further substituted with one or more branched or straight chain alkyl or alkenyl groups or one or more moieties selected from the group consisting of hydroxyl, oxyl, amino and alkoxyl, and wherein two or more such nitroxyl containing rings formed from $R_{10}$ plus $R_{11}$ may be joined by at least one linking group.

3. A composition as claimed in claim 2 wherein two or more such nitroxyl containing rings from $R_{10}$ plus $R_{11}$ are joined by at least one linking group, and wherein said at least one linking group is selected from the group consisting of $C_1$ to $C_{18}$ alkylene, $C_4$ to $C_{18}$ alkenylene, xylylene, a divalent acyl radical of an aliphatic, araliphatic or aromatic dicarboxylic acid, a divalent acyl radical of a dicarbamic acid, a divalent acyl radical of a phosphorous-containing acid, a divalent acyl radical of a sulphur containing acid, a bivalent silyl radical, a sulphone, a sulphide, a nitrogen containing group, and a bisether.

4. A composition as claimed in claim 2 wherein two or more such nitroxyl containing rings formed from $R_{10}$ plus $R_{11}$ are joined by at least one linking group, and wherein said at least one linking group is selected from the group consisting of an acyl radical of an aliphatic $C_2$ to $C_{36}$ dicarboxylic acid, an acyl radical of a $C_8$ to $C_{14}$ cycloaliphatic acid, an acyl radical of a $C_8$ to $C_{14}$ aromatic dicarboxylic acid, and an acyl radical of a $C_8$ to $C_{14}$ aromatic dicarbamic acid.

5. A composition as claimed in claim 2 wherein said at least one nitroxyl compound is selected from the group consisting of 4-hydroxy-2,2,6,6-tetramethylpiperidin-N-oxyl and 4-oxo-2,2,6,6-tetramethylpiperidin-N-oxyl.

6. A composition as claimed in claim 1 wherein said at least one quinone compound comprises 2,5-di-tertbutyl benzoquinone.

7. A composition as claimed in claim 1 wherein said at least one hydroxylamine compound comprises at least one aromatic hydroxylamine.

8. A composition as claimed in claim 1 wherein said at least one hydroxylamine compound comprises at least one aliphatic hydroxylamine.

9. A composition as claimed in claim 1 wherein the weight ratio of said at least one quinone compound of structure (i) to said at least one hydroxylamine of structure (ii) is in the range of from 9:1 to 1:9.

10. A composition as claimed in claim 1 wherein said ethylenically unsaturated compounds comprise vinyl aromatic monomers or other ethylenically unsaturated monomers.

11. A composition as claimed in claim 1 wherein said composition also contains one or more formulation adjuvants selected from the group consisting of solvents, cosolvents, solubilising agents, liquid carrying agents, emulsifiers and dispersants.

12. A composition as claimed in claim 11 wherein said one or more solvents, cosolvents or solubilising agents are selected from the group consisting of aromatic compounds, vinyl aromatic compounds and non-aromatic compounds.

13. A composition as claimed in claim 12 wherein said aromatic compounds, vinyl aromatic compounds and non-aromatic compounds are selected from the group consisting of toluene, ethyl benzene, styrene, alcohols and glycol ethers.

14. A composition as claimed in claim 11 wherein said non-aromatic compounds are selected from glycol ethers which include one or more alkyl ethers of diethylene glycol.

15. A process stream which comprises a retarder composition as claimed in claim 1 in combination with at least one ethylenically unsaturated compound.

16. A process stream as claimed in claim 15 wherein said at least one ethylenically unsaturated compound comprises at least one vinyl aromatic monomer or other ethylenically unsaturated monomer.

17. A vinyl aromatic monomer process stream as claimed in claim 16 wherein said vinyl aromatic monomer comprises styrene or divinyl benzene.

18. A process stream as claimed in claim 15, wherein the weight ratio of said retarder composition to said ethylenically unsaturated compound is in the range from 1:200 to 1:40000.

19. A composition as claimed in claim 7 wherein said at least one aromatic hydroxylamine comprises N,N-dibenzyl hydroxylamine.

20. A composition as claimed in claim 8 wherein said at least one aliphatic hydroxylamine comprises bis(hydroxypropyl) hydroxylamine.

21. A method for the prevention of unwanted polymerisation reactions during the production and processing of ethylenically unsaturated compounds, said method comprising treating a composition comprising at least one ethylenically unsaturated compound with a composition as claimed in claim 1.

22. A method as claimed in claim 21 wherein a composition as claimed in claim 1 is injected into a process stream comprising at least one ethylenically unsaturated compound.

* * * * *